US00PP11483P

United States Patent [19]

Austin

[11] Patent Number: Plant 11,483

[45] Date of Patent: Aug. 15, 2000

[54] SHRUB ROSE PLANT NAMED 'AUSCHAR'

[75] Inventor: David C. H. Austin, Wolverhampton, United Kingdom

[73] Assignee: David Austin Roses Limited, United Kingdom

[21] Appl. No.: 09/168,408

[22] Filed: Oct. 7, 1998

[51] Int. Cl.[7] ..... A01H 5/00

[52] U.S. Cl. ..... Plt./104

[58] Field of Search ..... Plt./102, 104, 145, Plt./134

[56] References Cited

U.S. PATENT DOCUMENTS

| | | | |
|---|---|---|---|
| P.P. 8,688 | 4/1994 | Austin | Plt./104 |
| P.P. 9,705 | 11/1996 | Austin | Plt./104 |
| P.P. 10,757 | 1/1999 | Austin | Plt./104 |

*Primary Examiner*—Howard J. Locker

*Attorney, Agent, or Firm*—Klarquist Sparkman Campbell Leigh & Whinston, LLP

[57] ABSTRACT

A shrub rose plant having a strong growing, disease resistant plant; and old-fashioned shaped, fragrant blooms which repeat well throughout the season.

1 Drawing Sheet

The present invention relates to a new and distinct variety of shrub rose plant of the rosa hybrida class which was originated by me by crossing the variety 'Graham Thomas', unpatented, with an unnamed seedling.

The primary objective of this breeding was to produce a new shrub rose variety having a strong growing, disease resistant plant with yellow, old-fashioned shaped, fragrant blooms which repeat well throughout the season. The objective was substantially achieved, along with other desirable improvements, as evidenced by the following unique combination of characteristics that are outstanding in the new variety and that distinguish it from its parents, as well as from all other varieties of which I am aware:

1. Very full, apricot-yellow flowers; and
2. Bushy growth habit.

Asexual reproduction of this new variety by budding, as performed at Albrighton, Wolverhampton, England, shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—'Graham Thomas' (unpatented).

*Pollen parent.*—Unnamed seedling of unknown parentage.

Classification:

*Botanical.*—*Rosa hybrida.*

*Commercial.*—Shrub.

FLOWER

Observations made from specimens grown in a garden environment at Albrighton, Wolverhampton, England, Jul. 18, 1995.

Blooming habit: Recurrent.

Bud:

*Size.*—About 1 to 1¼ inch long when the petals start to unfurl.

*Form.*—The bud form is short, pointed ovoid.

*Color.*—When sepals first divide, bud color is Orange Group 26B. When half blown, the outer petals on their upper sides are Yellow-White Group 158C on their outer portion, the color shading to Yellow Group 18D on the lower portion, and the inner petals on their upper sides are Yellow Group 18D, and the lower sides of the petals are Yellow Group 19D on the outer petals, and Yellow-Orange Group 22C on the inner petals. As the sepals begin to unfold, the outer petals are irregularly mottled with a red coloration approaching R.H.S. 31A.

*Sepals.*—Color: Yellow-Green Group 144B. Surface texture: Upper side hairy; underside slightly waxy and prickly. There are three lightly appendaged sepals and two unappendaged sepals with hairy edges.

*Receptacle.*—Color: Yellow-Green Group 144B. Shape: Pear. Size: Small (about ⅜ inch long×⅜ inch wide). Surface: Smooth.

*Peduncle.*—Length: Medium, averaging about 1½ to 2 inches. Surface: Prickly. Color: Yellow-Green Group 144B on the upper part and Greyed-Purple Group 183B on the lower part. Strength: Erect.

Bloom:

*Size.*—Large. Average open size is 3 to 3½ inches.

*Borne.*—Several together in pyramidal clusters of three or more blooms and singly.

*Stems.*—Normal strength. Average length is about 10 to 30 inches.

*Form.*—When first open: Bloom is cupped. Permanence: Outer petals curl back.

*Petalage.*—Number of petals under normal conditions: 90.

*Color.*—The upper sides of the petals are Yellow Group 8B, the outermost petals being Yellow Group 4D. The reverse sides of the petals are Yellow Group 11B. The base of each petal is Yellow Group 3B. The major color on the upper sides is Yellow Group 8B.

*Variegations.*—None.

*Discoloration.*—The general tonality at the end of the first day: Same. At the end of the third day: Fades to Yellow Group 11D.

*Fragrance.*—Moderate to strong tea fragrance with lilac and mimosa.

Petals:

*Texture*.—Leathery.

*Shape*.—Deltoid.

*Form*.—Moderately quilled towards the center.

*Arrangement*.—Irregular. Petaloids are few and small in the center. Petaloids are Yellow Group 8A.

*Persistence*.—Petals hang on and dry.

*Lastingness*.—On the plant: Long, about five days. As a cut flower: Not tested.

Reproductive parts:

*Anthers*.—Size: Medium. Quantity: Few. Color: Yellow-Orange Group 17B. Arrangement: Partly tucked in calyx.

*Filaments*.—Color: Yellow Group 13B.

*Pollen*.—Color: Yellow-Orange Group 15A.

*Styles*.—Color: Yellow-Green Group 145C.

*Stigmas*.—Color: Yellow Group 9A.

Form: Shrub.

Growth: Vigorous, upright, bushy. Mature plant is three feet in height and three feet in width.

Foliage: Number of leaflets on normal mid-stem leaves: Seven.

*Size*.—Medium. (5 to 8 inches long×3½ to 5½ inches wide.)

*Quantity*.—Normal.

*Color*.—New foliage: Upper side: Green Group 144A overlaid with Red-Purple Group 60A which disappears fairly quickly. Lower side: Yellow-Green Group 146B. Old foliage: Upper side: Green Group 137A. Lower side: Green Group 137C.

Leaflets:

*Shape*.—Pointed oval.

*Texture*.—Upper side: Leathery, semi-glossy.

*Edge*.—Serrated.

*Serration*.—Single, small.

*Petiole rachis*.—Color: Yellow-Green Group 144B.

*Petiole underside*.—Smooth with a few small thorns and bristles.

*Stipules*.—Short (about ½ to ¾ inch long), smooth with a few small thorns and bristles on the underside.

*Disease resistance*.—Resistant to mildew, blackspot and rust under normal growing conditions at Albrighton, Wolverhampton, England.

Wood:

*New wood*.—Color: Green Group 143B suffused with Greyed-Purple Group 183A. Bark: Smooth.

*Old wood*.—Color: Green Group 143A. Bark: Smooth.

Prickles:

*Quantity*.—On main canes from base: Ordinary. On laterals from main canes: Few.

*Position*.—Mainly lower end of stem, although there are some higher up.

*Form*.—Medium to short, hooked downward.

*Color when young*.—Greyed-Purple Group 185B, but brighter.

*Color when mature*.—Greyed-Orange Group 164C.

Small prickles:

*Quantity*.—On main stalks: Few. On laterals: None.

I claim:

1. A new and distinct variety of shrub rose plant, substantially as herein shown and described, characterized particularly as to novelty by the unique combination of its strong growing, disease resistant plant; and old-fashioned shaped, fragrant blooms which repeat well throughout the season.

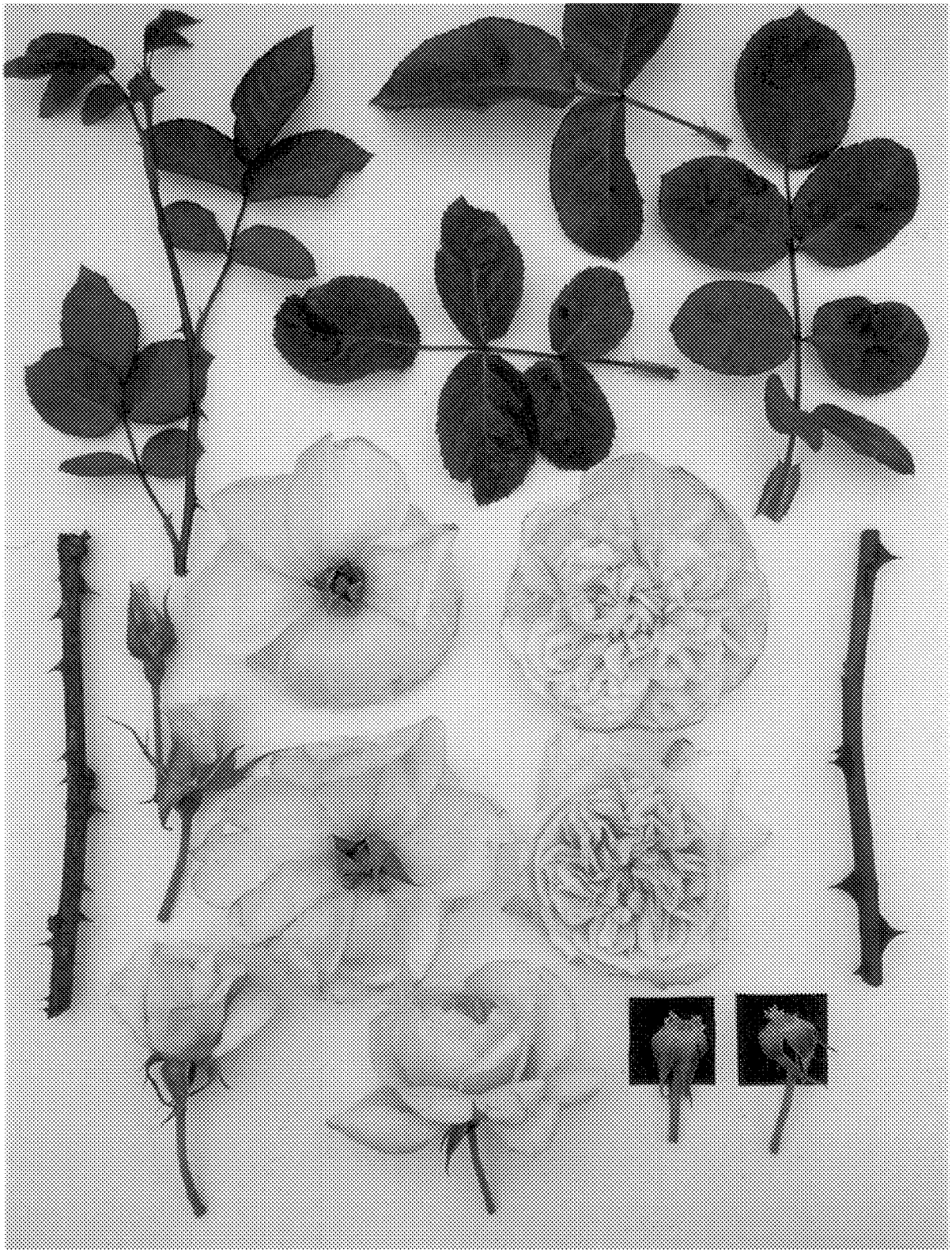

* * * * *